(12) United States Patent
Kalwa et al.

(10) Patent No.: US 9,759,653 B2
(45) Date of Patent: Sep. 12, 2017

(54) METHOD FOR DETERMINING THE MOISTURE CONTENT OF A RESIN LAYER ON A CARRIER BOARD

(71) Applicant: Flooring Technologies Ltd., Pieta (MT)

(72) Inventors: Norbert Kalwa, Horn-Bad Meinberg (DE); Andre Denk, Wittstock/Dosse (DE)

(73) Assignee: Flooring Technologies Ltd., Pieta (MT)

( * ) Notice: Subject to any disclaimer, the term of this patent is extended or adjusted under 35 U.S.C. 154(b) by 0 days.

(21) Appl. No.: 14/893,794

(22) PCT Filed: May 28, 2014

(86) PCT No.: PCT/EP2014/061123
§ 371 (c)(1),
(2) Date: Nov. 24, 2015

(87) PCT Pub. No.: WO2014/191491
PCT Pub. Date: Dec. 4, 2014

(65) Prior Publication Data
US 2016/0123871 A1 May 5, 2016

(30) Foreign Application Priority Data
May 30, 2013 (EP) .................................... 13169864

(51) Int. Cl.
*G01N 21/35* (2014.01)
*G01N 21/3554* (2014.01)
(Continued)

(52) U.S. Cl.
CPC ....... *G01N 21/3554* (2013.01); *G01N 21/359* (2013.01); *G01N 21/3563* (2013.01);
(Continued)

(58) Field of Classification Search
CPC ........... G01N 21/3554; G01N 21/3563; G01N 21/359
See application file for complete search history.

(56) References Cited

U.S. PATENT DOCUMENTS

| 2003/0048440 A1* | 3/2003 | Lindgren ........... G01N 21/3554 356/300 |
| 2004/0191547 A1* | 9/2004 | Oldorff .................. E04F 15/02 428/479.3 |

(Continued)

FOREIGN PATENT DOCUMENTS

| DE | 102008041052 A1 | 2/2010 |
| EP | 0310350 A2 | 4/1989 |

(Continued)

*Primary Examiner* — Casey Bryant
(74) *Attorney, Agent, or Firm* — The Webb Law Firm (57) ABSTRACT

A method for determining the moisture content of at least one resin layer provided on at least one wooden board as carrier board, wherein between the at least one resin layer and the carrier board an NIR reflecting layer is provided, including recording of at least one NIR spectrum of the at least one resin layer provided on the at least one carrier board using a NIR detector in a wavelength range between 500 nm an 2500 nm; determining the moisture content of the resin layer by comparing the NIR spectrum recorded for the resin layer to be measured with at least one NIR spectrum recorded for at least one reference sample with known moisture content by means of a multivariate data analysis, wherein the at least one NIR spectrum recorded was determined previously using the same NIR detector in a wavelength range between 500 nm and 2500 nm.

20 Claims, 4 Drawing Sheets

(51) Int. Cl.
*G01N 21/359* (2014.01)
*G01N 21/3563* (2014.01)
*E04F 13/16* (2006.01)
*E04F 15/10* (2006.01)

(52) U.S. Cl.
CPC ............... *E04F 13/16* (2013.01); *E04F 15/10* (2013.01); *G01N 2201/129* (2013.01)

(56) References Cited

U.S. PATENT DOCUMENTS

| | | |
|---|---|---|
| 2007/0131862 A1 | 6/2007 | Cowan et al. |
| 2009/0017223 A1 | 1/2009 | Price |
| 2011/0199098 A1 | 8/2011 | Bense et al. |
| 2013/0240137 A1 | 9/2013 | Kalwa |
| 2013/0291792 A1 | 11/2013 | Oldorff |

FOREIGN PATENT DOCUMENTS

| | | |
|---|---|---|
| EP | 1454763 A2 | 9/2004 |
| EP | 2338693 A1 | 6/2011 |
| EP | 2452829 A1 | 5/2012 |

\* cited by examiner

METHOD FOR DETERMINING THE MOISTURE CONTENT OF A RESIN LAYER ON A CARRIER BOARD

CROSS-REFERENCE TO RELATED APPLICATIONS

This application is the United States national phase of International Application No. PCT/EP2014/061123 filed May 28, 2014, and claims priority to European Patent Application No. 13169864.9 filed May 30, 2013, the disclosures of which are hereby incorporated in their entirety by reference.

BACKGROUND OF THE INVENTION

Field of the Invention

The present invention relates to a method for determining the moisture content of a resin layer on a carrier board and the use of an NIR (Near Infrared) detector for determining the moisture content of a resin layer on a carrier board.

Description of Related Art

Wooden boards as carrier materials are used in different areas and are widespread. Thus, wooden boards are known amongst others for their use as floor panels, for instance in form of laminate floors, as insulation boards for internal and external area or also as wall panels. Such boards are usually made from wood fibers, wood ships or strands. In case of laminate floors, for instance HDF boards (HDF=fiber board with increased wall density) made of wood fibers are used with diverse decors and protective layers applied thereon.

The use of the so called overlay papers as protective or wear resistant layer is for instance known. Said overlay papers are thin papers typically impregnated with a melamine resin, wherein wear resistant particles as for instance corundum particles are mixed into the resin of the overlay in order to increase the wear resistance of the laminate or the wooden board. Besides the use of said overlay papers as wear resistant layer in another variant a powder is applied to the surface of the board, which comprises for instance natural or synthetic fibers, wear resistant particles and binder. Also in this case, the wear resistance and stability of the surface of the board is increased by using in particular wear resistant particles.

Besides the above-mentioned wear resistant layers in form of an overlay paper or a powder with wear resistant particles, the application of a liquid resin as protective layer is also known, in which also wear resistant particles as for instance corundum particles or glass balls can be contained. Such a liquid resin layer is also known as liquid overlay (EP 2 338 693 A1).

When producing wooden boards by using a liquid overlay an important criteria for quality insurance is the determination of the moisture during the coating process. When coating wooden boards, as for instance wooden boards provided with a printed décor layer, with water containing duroplastic resins, as for example urea or melamine resins, the water of the resin has to be reduced to a defined percentage by convection and/or a radiation, for instance by means of infrared (IR) and/or near infrared (NIR) radiation. The water to be removed stems on the one hand from the aqueous resin solution and on the other hand additional water results from the curing of the resin due to the condensation reaction. This water content has to be in a relative small range, since otherwise quality problems can occur during processing or in the final product.

The basic problem which arises during moisture determination of boards with liquid structure is the relative unfavourable ratio between applied resin water amount and the total weight of the coated board. This ratio is about 1:30 to 1:50 that means the applied liquid overlay layer is provided in very thin layers. Due to the percentage of the liquid overlay, which is small in respect to the weight, it is difficult to determine the moisture reduction for instance gravimetrically. Such a method is used for instance when determining the residual moisture of papers impregnated with thermosetting resins. There, the ratio between carrier (paper) and resin is about 1:1.

The determination of the moisture of a resin layer, which is applied as liquid overlay on a wooden board, using the so called Darr sample is also not possible. The Darr sample method is the most accurate method for determining wood moisture, wherein a sample is dried at 103+/−2° C. for 24 hours in a drying oven. The wood moisture is defined as the ratio of the weight of the water contained in the wood to the weight of the absolute dry wood (Darr weight). The wood moisture is therefore a ratio between wet weight and dry weight (Darr weight).

When using the Darr probe for a wooden board coated with a liquid overlay not only the moisture of the liquid overlay coating would be determined, but also the moisture of the wooden board, so that only a value of the total moisture of board and coating would be obtained. The Darr sample or the Darr method would also not allow a short-term change or interference in the drying process within the production line due to the drying process of 24 hours. Furthermore, such a moisture determination can also only be carried out using a final coated board after leaving the production line and due to this reason allows thus also no interference into the production process.

Also the possibility of sealing the wooden board, more exactly, the wooden carrier board by a water non-permeable foil would not be suitable for solving this problem, since the coating system would let pass moisture rising from the HWS carrier from the board.

The technical object of the present invention is thus to provide a method, which allows the determination of the moisture content of a resin layer, for instance a liquid overlay, provided on a wooden board which allows a sufficiently exact determination of the moisture and whereby quality deficiencies, which can be addressed to the moisture content of the resin layer, can be turned off.

SUMMARY OF THE INVENTION

Accordingly, a method for determining the moisture content of at least one resin layer provided on at least one wooden board as carrier board is provided, wherein between the at least one resin layer and the carrier board an NIR reflecting layer is provided. The present method comprises the following steps:

Recording of at least one NIR spectrum of the at least one resin layer provided on the at least one carrier board using an NIR detector in a wavelength range between 500 nm and 2500 nm, preferably between 700 nm and 2000 nm, in particular preferably between 900 nm and 1700 nm;

determining the moisture content of the resin layer by comparing the NIR spectrum recorded for the resin layer to be measured with at least one NIR spectrum recorded for at least one reference sample with known moisture content by means of a multivariate data analysis (MDA), wherein the at least one NIR spectrum recorded for the at least one reference sample with known moisture content was determined previously using the same NIR detector in a wavelength range between 500 nm and 2500 nm, preferably between 700 nm and 2000 nm, in particular, preferably between 900 nm and 1700 nm.

In an embodiment of the present method, a further layer—also designated as priming layer or NIR reflecting layer—is provided between the at least one resin layer and the carrier board as for example a wooden board. The composition or quality of this further reflecting layer is explained in more detail further below.

The present method allows accordingly the determination of the moisture or the moisture content of a resin layer, for example a liquid overlay, which is applied to the surface of a carrier board for instance a wooden board, immediately following the coating and/or drying thereof in known coating and drying devices. It is of particular advantage that by using the NIR detector a moisture determination in a thin resin layer can be conducted, which is arranged on a carrier board.

The moisture content of the resin layers to be measured has preferably values of maximum 15 weight %, preferably maximum 10 weight %, in particular preferably maximum 8 weight %. It is in particular preferred, if the moisture content of the resin layer to be determined is between 4 and 8 weight %.

NIR detectors allow the determination of moisture or the water content in different materials, as for instance resins, wood materials, wood pellets, grains and so on. Using this type of measurement multiple hundred NIR measurements are carried out in a few tenths of a second such that also a statistical assurance of the measured values is guaranteed. It is thereby essential that in case of a calibration using Darr samples real moisture values are compared to spectroscopically determined values. In case of grains or wooden pellets this is easily done since the total moisture shall be determined. When determining the moisture in a coating system on a wooden material, as presently in case of a liquid overlay on a wooden board, the described method fails due to the additional water vaporizing from the carrier material.

This is not only valid for all wooden boards, but also for carrier materials, which contain residual moistures. All of these can be used as carrier for decorative upgradings in different applications. They are typically printed and provided with wear resistant layers on the basis of aqueous resins. In particular, these can be chip boards, fiber boards, OSB boards, plywood, magnesium oxide boards, wood plastic composites, plastic boards, cement chip/fiber boards and gypsum fiber boards. This list can be extended as wished and does not claim any completeness.

In an embodiment, a wooden board in form of a medium density fiber (MDF), high density fiber (HDF) or oriented strand (OSB) or plywood panel, a cement fiber board and/or gypsum fiber board is used as a carrier board or as carrier material.

The present method for determining the moisture content of a resin layer, which is arranged on a carrier board as for instance a wooden board, by using a NIR detector uses in contrast the fact that the NIR radiation does not penetrate through the complete board, that means through resin layer and carrier board, but is reflected on the surface of the wooden board, in particular on the NIR reflecting layer as print or priming layer. The NIR radiation penetrates therefore in the present method only and exclusively through the resin layer, for instance liquid overlay layer and is reflected back from the surface of the wooden board, in particular from the NIR reflecting layer as the print. The reflected NIR radiation is absorbed by the resin layer in a characteristic manner and the recorded NIR spectrum is used for determining the moisture content.

A NIR spectrum recorded for a resin layer, as for instance a melamine resin, has a clear broad absorption band with an absorption maximum at about 1490 nm. This band is amongst others typical for a melamine resin and corresponds to the first harmonic of NH groups. Furthermore, a water band at about 1400 nm is also typically present. Due to the overlapping of both bands the water band appears as a shoulder of the broad band.

A different moisture content of the resin layer can be in particular recognized by means of the height of the baseline of the NIR spectrum, whereas the shapes of the NIR spectrums hardly differ from each other. A linear relationship between the absorption value at the band maximum at about 1490 nm and the moisture content according to the equation (I) y=mx+n is not detectable, what is most likely due to the intensity degrees of the absorption band of NH groups by a progressing polycondensation of the resin.

Accordingly, the comparison and interpretation of the NIR spectrums are done over the complete recorded spectral range. This is done by the multivariate data analysis MDA. Multivariate analysis methods typically analyze multiple statistical variables. For this reason, the number of variables included in a data set is reduced without reducing at the same time information included therein.

In the present case, the multivariate data analysis is carried out using the method of the Partial Least Squares (PLS) regression wherein a suitable calibration model can be established. The evaluation of the collected data is carried out preferably with a suitable analysis software, as for instance with the analysis software SIMCA-P of the company Umetrics AB.

It is preferred, if the reference sample with a known moisture content comprises at least one resin layer, in particular pre-dried resin layer, applied to a priming layer (or NIR reflecting layer) of a carrier board, for instance wooden board. The resin layer, optionally priming layer and carrier board of the reference sample are thereby preferably similar to the sample of resin layer, optional priming layer and carrier board to be measured. In other words, the resin layer of the reference sample has the same composition as the resin layer to be measured. The same is applicable for the optionally used priming layer and the carrier board.

The similarity of the sample to be measured and reference sample is in particular important when using resin layers with additives such as flame retardants, fibers, carbon nanotubes and further additives. The addition of additives to the resin layer results typically in additional peaks in the NIR spectrum and eventually in a shift of the baseline. Accordingly, a new calibration or establishment of a new calibration model using a similar reference sample is required.

The relationship between moisture content of a resin layer and the NIR spectrum of said resin layer is preferably determined as described in the following.

First, a first sample, for instance in form of a printed board with a pre-dried resin layer is dried in a drying oven, for instance at 103+/−2° C. for 2 hours and after cooling of the dried sample under moisture exclusion a measurement with the NIR detector is carried out. The NIR spectrum used for a completely dried sample (Darr sample) is used as zero value.

Subsequently, carrier boards provided with a resin layer and pre-dried are sprayed with a defined amount of water, which distributes in the resin matrix. The carrier boards sprinkled or sprayed with water are measured in a NIR detector and the NIR spectrums for these carrier boards sprayed with a defined amount of water are determined. Due to the high number of measurements within a few tenths of seconds a possibly present uneven distribution of the sprayed water is eliminated.

Subsequently, a suitable calibration model is established, preferably in the manner described in the following. At first, a calibration model is established from the spectrums of the samples with known moisture content (that means, the carrier boards sprinkled with water) by using the partial least squares (PLS) regression. This model is used for determining the residual moisture in the Darr sample. Using said calibration model a moisture content for the Darr sample (dried carrier board with resin layer) is calculated by the analysis program, wherein a negative moisture value or moisture content results for the Darr sample. Subsequently, the amount of the moisture content for the Darr sample is added to all used moisture values of the carrier boards sprinkled with water (calibration samples) and the moisture content of the Darr sample is set to zero. Based on these new calibration values of the moisture and the measured NIR spectrums, a new calibration model is established by means of the partial least squares (PLS) regression, which establishes a relationship between the measured NIR spectrums of a resin layer to be measured on a carrier board, for instance a wooden board and the NIR spectrums of reference samples with known moisture content. This second calibration model can be used for predicting the moisture content of the measured NIR spectrums of unknown samples.

In case of the above-described calibration model it has to be taken into account that it is not essential to determine the absolute moisture content of a resin layer, but that it rather offers the possibility to correlate the moisture content of a resin layer to the quality properties of the final product. This means that the determined moisture values are not to be considered as absolute exact moisture values, but as approximate values. This allows then the development and carrying out of measurements for improving quality and/or process control of a production line of boards, for instance wooden boards. For instance, the dryer performance or the feed in case of an insufficient drying of a resin layer can be adapted. Furthermore, due to the availability of NIR measurement values an error search based on the principle of exclusion can also be carried out, what was not possible before.

In an embodiment of the present method, the resin layer to be measured consists of at least one formaldehyde containing resin, in particular a melamine formaldehyde resin, a urea formaldehyde resin or mixtures of both. Furthermore, the use of aqueous polyurethane (PU) or acrylate systems is possible.

The amount of the resin layer to be measured can be between 10 to 150 g solid resin/$m^2$, preferably between 20 and 100 g solid resin/$m^2$, in particular preferably between 40 and 60 g solid resin/$m^2$.

It is also possible that the resin layer to be measured comprises wear resistant particles, natural and/or synthetic fibers and further additives. The resin layer to be measured is typically applied in form of a liquid resin suspension of the above-mentioned resins with the appropriate supplements on the surface of the wooden board.

The natural or synthetic fibers used in the resin layer (liquid overlay) are preferably selected from the group containing wood fibers, cellulose fibers, partially bleached cellulose fibers, wool fibers, hemp fibers and organic or inorganic polymer fibers.

The wear resistant particles of the liquid overlay are preferably selected from the group containing aluminum oxide, corundum, boron carbide, silicon dioxide, silicon carbide and glass balls, wherein corundum particles, glass/hollow balls or glass particles are in particular preferred.

As already mentioned above, at least one additive can be added to the heat curable resin layer, which can be selected from the group containing conductive substances, flame retardants or luminescent compounds. The conductive substances can be selected from the group containing carbon black, carbon fibers, metal powder and nanoparticles, in particular carbon nanotubes. A combination of these substances can also be used. As flame retardants, for instance phosphates, borates, in particular ammonium polyphosphate, tris(tri-bromeneopentyl)phosphate, zinc borate or boron acid complexes of polyvalent alcohols can be added to the resin layer. The use of flame retardants provides a reduction of flammability and is therefore in particular of importance in case of laminate floors, which are used in closed rooms with particular requirements to the fire protection or in emergency escape roads.

As already mentioned above, the NIR spectrums can be altered by additional peaks due to the addition of flame retardants, fibers and further additives. There can also be a shift of the baseline of the NIR spectrums, what has to be considered accordingly when establishing the calibration model. Therefore, it is required when using additives in the resin layer to establish a calibration model by using a reference sample, which comprises the same additives in the resin layer.

In order to improve the flame retardation appropriate flame retardants can be added of course also to the carrier boards, in particular the wooden boards.

As luminescent compounds preferably fluorescent and/or phosphorescent compounds of inorganic or organic basis, in particular zinc sulfide and earth alkali aluminate are preferably used. The luminescent compounds can be applied in geometrical shapes on the surface using templates. Due to the incorporation of these dies into the surface of wooden boards, which can be used for instance in closed rooms as floor or wall panels, information of escape roads and escape directions is possible in case of a light failure.

In an embodiment, the resin layer to be measured comprises more than one layer, for instance at least two layers of a resin. Thus, the resin layer to be measured can consist of three resin layers, or comprise three resin layers, wherein in one of the three resin layers wear resistant particles, for instance corundum particles, are present, in a second resin layer of the three resin layers natural and/or synthetic fibers, as for instance cellulose fibers, are present and in a third resin layer of the three resin layers again wear resistant particles, as for instance glass particles can be present. In a particular preferred embodiment, the layer of the resin layer containing corundum particles is applied to the wooden board as a first layer, subsequently, the second resin layer containing the cellulose fibers is applied and finally the third resin layer containing glass particles is applied as most upper layer of the resin layer. The first resin layer can contain 15 to 25 weight %, preferably 20 weight % corundum particles, the second resin layer 3 to 7 weight %, preferably 5 weight % cellulose fibers and the third resin layer 15 to 25 weight %, preferably 20 weight % glass particles.

A method for obtaining the described liquid overlay coating is described amongst others in EP 2 338 693 A1. Hereby, at first, after purifying the upper and/or lower side of a wooden board, a first upper resin layer containing corundum particles is applied to the upper side and/or lower side of the wooden board, said first resin layer is dried for instance to a residual moisture of maximum 10 weight %, preferably 4 to 8 weight %, subsequently a second resin layer containing cellulose fibers is applied to the upper side and/or lower side of the wooden board, the second layer is again dried or pre-dried to a residual moisture of maximum 10 weight %, preferably of 4 to 8 weight %, at least one third resin layer containing glass particles is applied to the upper side and/or lower side with subsequent pre-drying of the third resin layer, for instance also to a residual moisture of maximum 10 weight %, preferably of 4 to 8 weight % and finally the layer construction is pressed under pressure and temperature influence. By using a liquid overlay the otherwise typically provided overlay paper can be dispensed.

As already mentioned above, at least one NIR radiation reflecting layer is arranged between the resin layer to be measured and the wooden board—more exactly the surface of the wooden board.

The at least one NIR reflecting layer can be selected from at least one first resin layer (for instance colorless melamine-formaldehyde-resin layer, melamine-urea-formaldehyde resin layer), which is directly provided on the surface of the carrier board; a white priming layer which is optionally provided with pigments; a décor or printing layer and/or at least one layer of radiation curable filling compound or a further protective layer of radiation curable lacquer or water compatible resin.

In a variant, said NIR reflecting layer can comprise preferably a white priming layer, at least one décor or printing layer printed on the wooden board and/or at least one layer of radiation curable filling compound or radiation curable lacquer.

It is also possible that the at least one NIR reflecting layer comprises a layer construction of more than one, preferably of two, three or four NIR reflecting layers. Thus, it is provided in one embodiment that the NIR reflecting layer comprises a layer construction on the carrier board of at least one colorless resin layer or resin application, white priming layer, décor layer and protective layer. When using such a layer construction as NIR reflecting layer the NIR radiation is reflected preferably by each of the singular layers in a certain intensity and angle. Since the NIR reflection depends on the layer construction and also on the performance of the NIR radiation source the establishment of a reference spectrum under the exact same conditions (i.e. with the same layer construction) is required, as previously described.

In case of a décor layer, a water-based pigmented printing color can be applied in gravure printing or digital printing. The printing color can thereby be applied either directly on the non-treated surface of the wooden board or also on a provided priming layer. Said water-based pigmented printing color can also be applied in more than one layer, for instance 3 to 10 layers, preferably 5 to 8 layers, wherein the printing color is dried after each layer application, for instance in a convection dryer or an NIR dryer.

The problem, when detecting moisture by NIR is that the detector is color sensitive. This means that in case of prints on the board having the same moisture in the resin supernatant, but strongly deviate in their whiteness, different moisture values are detected. Therefore, in case of using prints as reflecting base layer or priming layer clusters of décors are created in each case for the purpose of calibration, which have a similar color position or color schemes. The use of multivariate data analysis (MDA) is shown also in this case to be helpful. The calibration spectra of different clusters can be assembled to a calibration model by means of PLS regression by which all samples can be measured without additional calibration. Herewith, the problem of a color sensitivity of the NIR detector is solved.

In case of using a printed décor layer as reflecting layer at least one protective layer, for instance of a resin or radiation curable lacquer is provided preferably on the same. Said protective layer serves in particular for protecting the décor in case of an intermediate storage of the printed carrier boards before further processing by applying the liquid overlay layer. The protective resin can be a water compatible resin, preferably a formaldehyde containing resin. The resin protective layer arranged on the décor layer is typically pre-dried in a continuous drying oven. If the protective layer applied to the décor layer consists on the other hand of radiation curable lacquer, as for instance from the group a acrylates, modified acrylates and/or epoxides, the curing and drying of the same occurs by using UV or electron radiation. The protective layer provided on the décor layer is present before the further processing preferably in a pre-dried and/or pre-gelled form.

As mentioned, it is also possible to coat or prime the carrier board as for instance a wooden board with a UV filler and/or ESH filler before printing and/or the application of the liquid overlay layer. A UV filler mass consists preferably essentially of UV curable lacquer components, pigments, reactive diluting agent and radical former as chain starter. It is also possible that the filler mass used for priming is pigmented. It can also be possible to apply the filler mass in multiple layers.

In case of using wooden boards as carrier boards, as for instance a medium density fiber (MDF), high density fiber (HDF) or oriented strand (OSB) or plywood panel, a cement fiber board and/or gypsum fiber board, said boards contain formaldehyde containing resins, such as melamine-formaldehyde resin, urea-formaldehyde resin or mixtures of both or phenol-formaldehyde resins as binder.

The present method for determining the moisture content can be applied in summary for a carrier board, in particular for a wooden board with the following structure:
- carrier board, for instance as wooden board of wood fibers,
- at least one NIR-reflecting layer or priming layer, wherein the at least one priming layer consists of a colorless resin application, a white priming layer, a décor layer, a further protective layer of filler mass, wherein also more than one of these layers can be provided as NIR reflecting layer;
- optionally, in case a decor layer as priming layer according to b), in particular a pre-dried or pre-gelled protective layer of a resin or a curable lacquer is arranged on the décor layer, and
- resin layer to be measured (overlay layer) can consist of multiple resin layers, for instance up to three resin layers and more.

It is also important to mention that the resin layer to be measured can be arranged on the upper side as well as also on the lower side of the carrier board, in particular the wooden board.

In a variant of the present method, the moisture content of the resin layer is carried out by using the at least one NIR detector after applying the resin layer for instance by means of rolling on the carrier board and a subsequent drying step in a drying segment, for instance in a convection dryer, IR and/or NIR dryer. Accordingly, at least one NIR detector is arranged in a production line of wooden boards in processing direction behind an application device and a drying device.

In case that the resin layer to be measured consists of multiple layers (resin layers), which are applied in respective separate process steps—as described above—the determination of the moisture content of each singular resin layer takes place in each case after applying and drying said resin layer. Thus, in a variant of the resin layer with three resin layers, the moisture content is determined in each case after applying the first layer, the second layer and the third layer. Thereby, it is possible to adapt and adjust the moisture content of the resin layers or the final resin layer already during the production process in the production line of the wooden boards.

The present method for determining the moisture content of a resin layer provided on a board has multiple advantages. The method allows a damage-free continuous measurement of the moisture in the surface (online measurement). Furthermore, the color influence on the measured values is eliminated and moistures in resin layers in a mass range between 10 and 150 g solid resin/m$^2$ can be measured. The present method allows also the use of an automatic control system with alarm message.

The present method for determining the moisture content of at least one resin layer provided on at least one wooden board as carrier board is conducted in a device or production line for producing boards, which comprises at least one application device, at least one drying device and at least one NIR detector for conducting the method according to the invention, wherein the at least one NIR detector is arranged in processing direction after the applying device and the drying device.

The at least one NIR detector is therefore arranged in a production line of the at least one board, comprising at least one applying device for the resin layer, as for instance a drum, spraying device or pouring device, and at least one drying device, for instance in form of a convection dryer, IR and/or NIR dryer.

The NIR detector can be installed at any position following the dryers. Thereby, the detector can also traverse over the board width or analyze specific problem areas (for instance overdrying in the edge or central area of the boards and so on). Furthermore, the measured values are readily available and allow an immediate interference in the process. This is not readily possible in case of other methods.

In an embodiment the device or production line for producing the wooden boards comprises more than one applying device and more than one drying device, wherein at least one NIR detector is arranged in processing direction after an applying device and a drying device, respectively.

In a preferred embodiment the arrangement of a production line is as follows:

a) a first applying device for applying a first resin layer to the upper side and/or lower side of the carrier board, wherein the first resin layer can contain for instance wear resistant particles in form of corundum particles,
b) a first drying device arranged in processing direction after the first applying device for drying the first upper and/or lower resin layer to a residual moisture of 6 to 9 weight %,
c) a first NIR detector arranged in processing direction after the first drying device,
d) a second applying device arranged in processing direction after the first NIR detector for applying a second resin layer, which can contain for instance cellulose fibers, to the upper side and/or lower side of the carrier board,
e) a second drying device arranged in processing direction after the second applying device for drying the second upper and/or lower resin layer to residual moisture of 6 to 9 weight %,
f) an NIR detector for determining the moisture content of the applied resin layers arranged in processing direction after the second drying device,
g) a third applying device arranged in processing direction after the second NIR detector for applying a third resin layer, which may contain for instance glass particles as wear resistant particles, to the upper side and/or lower side of the carrier board,
h) a third drying device arranged in processing direction after the third applying device for drying the third upper and lower resin layer to a residual moisture of 4 to 8 weight %,
i) at least one NIR detector arranged in processing direction after the third drying device for determining the moisture content of the applied resin layers, and
j) a short cycle press.

The applying devices are preferably double applying devices, which allow the application of the resin layers to the upper side and the lower side of the wooden board.

The solid content of the liquid resin layer (liquid overlay) to be applied is between 30 and 80 weight %, preferably between 50 and 65 weight %.

Depending on the requirements of the production line it is of course also possible to vary the number of the applying devices, drying devices with the respective NIR detector. Thus, it is for instance conceivable and possible to use a production line of two units comprising applying device, drying device and NIR detector or also more than three, as for instance four or five units as applying device, drying device and NIR detector.

It is, however, also conceivable and possible, in particular for the purpose of simplification and for cost reduction, to design a production line such that a NIR detector is provided after the last applying device and drying device. In such a case, the moisture content of the applied resin layers is only determined after the last drying device.

Following the last NIR detector a short cycle press is preferably arranged in processing direction, in which the resin layer or resin layers are cured under pressure and temperature. During this final pressing under pressure and temperature influence the resin layers melt and the linking process continues. This guarantees that the singular resin layers are not only linked within itself, but also linked amongst each other and thus can be pressed to a laminate. The short cycle press operates usually for instance at a pressure of 30 to 60 kg/m$^2$ and a temperature of 150 to 220° C., preferably 200° C. The pressure time is typically 5 to 15 seconds, preferably 6 to 12 seconds. Structured press plates are typically used in the short cycle press, by means of which additional structures can be impressed into the resin layers.

DESCRIPTION OF THE INVENTION

Example

The already primed wood fiber boards presently provided with a print and with a resin protective layer are separated in the production line and are coated with a liquid resin layer (liquid overlay). The liquid overlay can be a melamine-formaldehyde resin, a urea-formaldehyde resin or mixtures of both resins. The application of the liquid overlay layer is done preferably by means of rolling, spraying or pouring or a combination of the mentioned application methods. The application of the resin mixture using a roller device is however preferred. Wear resistant particles, additives such as wetting agent, separating agent hardener and other components such as glass balls or cellulose can be added to the liquid overlay layer.

The solid content of the liquid resin layer (liquid overlay) to be applied is between 50 and 65 weight %. The liquid overlay is preferably applied onto the upper side as well as to the backside of the wooden board, wherein the application to the backside of the wooden board is done also by using a roller device.

After the liquid overlay is applied the wooden board passes through a drying segment, which can consist for example of a convection, an IR or a NIR dryer or a combination thereof. In this drying segment a reduction of the moisture in the resin matrix to a value of maximum 10%, preferably a value between 6 to 9 weight % occurs. The residual moisture of the resin matrix that means the moisture content of the applied resin layer (liquid overlay) is determined after drying by using at least one NIR detector.

Subsequently, the wooden board passes further rolling applying devices and drying devices for the purpose of applying further resin layers. In the further applying devices a liquid resin layer is again applied, which can also contain the mentioned wear resistant particles and fibers and further additives or also colorants. An application of the resin layer to the backside of the wooden board can also take place in the further applying device. After application and intermediate drying of the further resin layer moisture measurement can follow once more. The application of the resin layer with subsequent drying can be repeated multiple times, what is also valid for the measurement of the moisture. After the last resin application a final determination of the moisture content of the resin layer using a NIR detector can be carried out. Thereby, the moisture content should be below 8%, preferably at values between 4 to 8 weight %. It is also conceivable for simplification and thus for cost reduction of the whole process to determine the moisture content of the applied resin layers only after the last drying device. After all resin layers are applied to the priming layer of the wooden board, the such coated wooden board is passed to a short cycle press and the resin layer is cured in said short cycle press under pressure and temperature.

By using suitable chromed and structured steel plates in the short cycle press it is possible to engrave defined structures into the resin surface of the wooden board. After pressing the typical quality parameters such as curing and porosity are determined. In case of deviations from the desired quality an improvement of the resin layer ("liquid overlay") can be effected by adapting the process parameters.

Figure 1A:
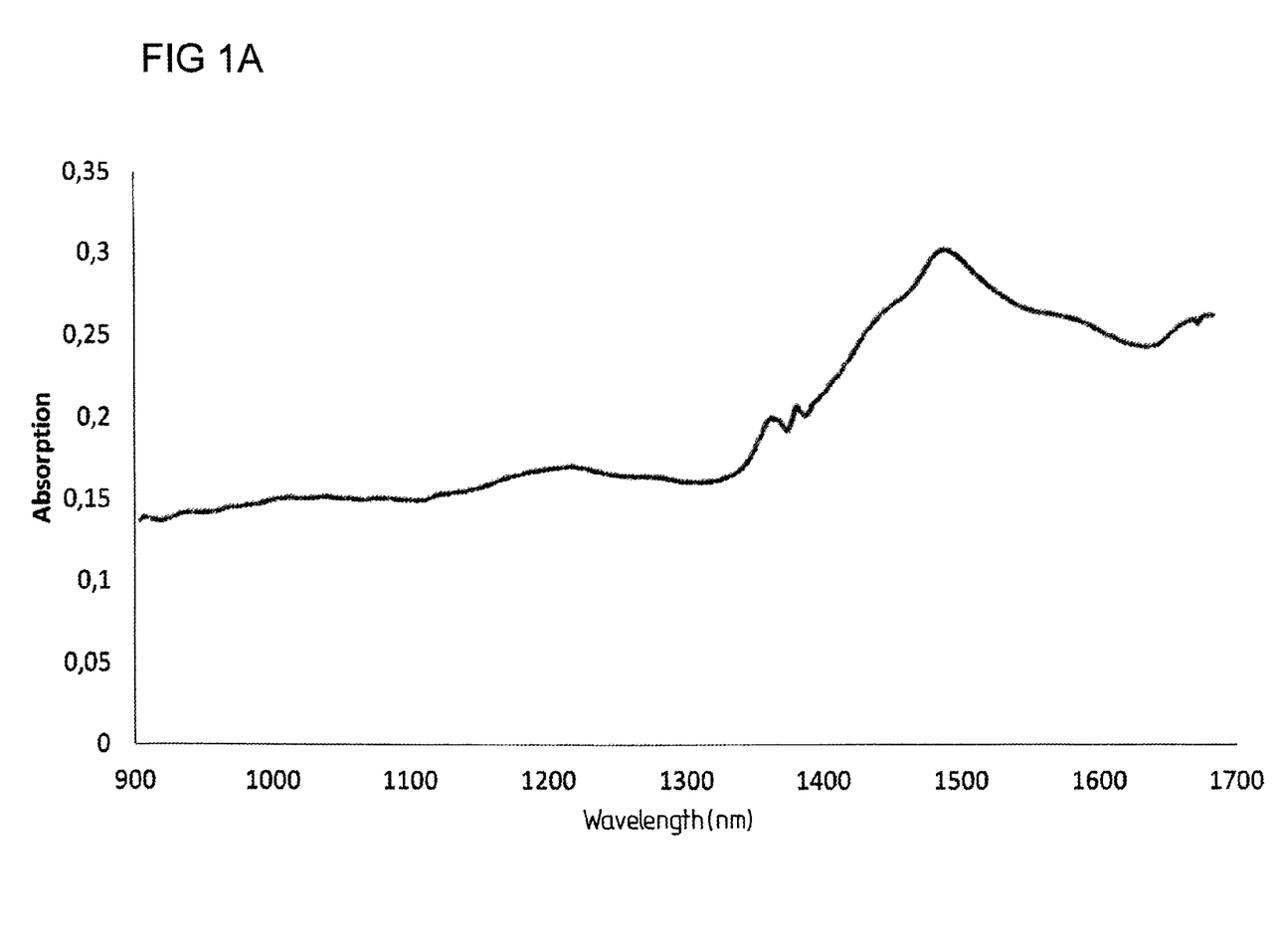
FIG. 1a is a diagram with a NIR spectrum measured for a first resin layer with unknown moisture content.

The diagram of FIG. 1a shows a typical NIR spectrum of a melamine formaldehyde resin layer according to the example. The NIR spectrum was recorded at present in a wavelength range between 900 and 1700 nm. For recording the NIR spectra a NIR measurement device of the company Perten was used. The measurement head carries the designation DA 7400.

Figure 1B:
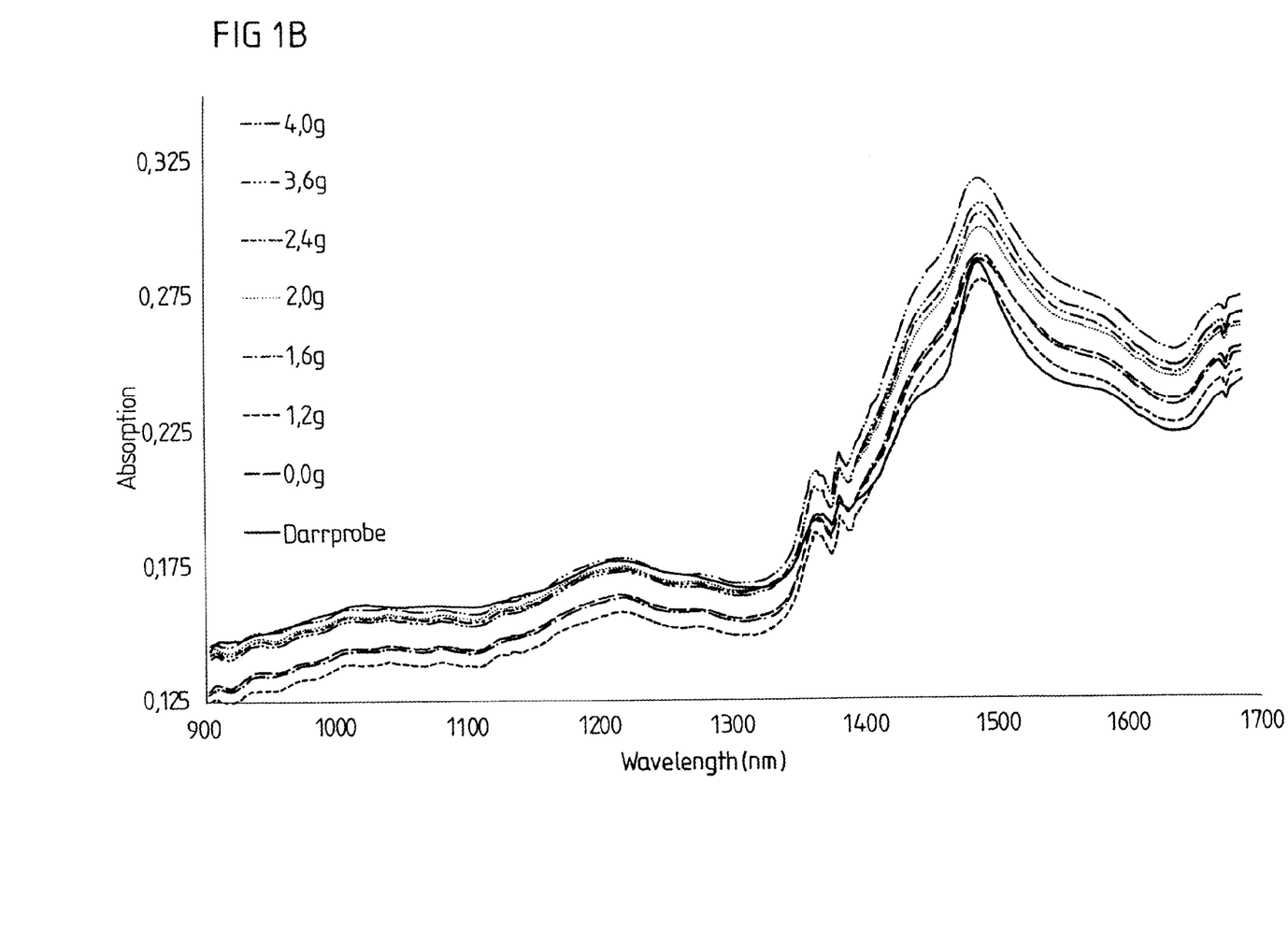
FIG. 1b is a diagram with NIR spectra of reference samples with different moisture content in each case for establishing a calibration model according to the principles of the present invention.

The diagram of FIG. 1b shows NIR spectra of reference samples with different moisture content. It can be seen that the NIR spectra differ in particular in the heights of the baseline. The higher the moisture content, the higher the base line and thus also the absorption value for the absorption maximum at 1490 nm, as illustrated in the following table.

TABLE 1

Correlation of moisture content and NIR-absorption maximum

| Moisture ($g/m^2$) | Absorption maximum at 1490 nm |
|---|---|
| 4 | 0.3175 |
| 3.6 | 0.3084 |
| 2.4 | 0.3047 |
| 2.0 | 0.3004 |
| 1.6 | 0.2894 |
| 1.2 | 0.2795 |
| 0 | 0.2885 |

Thus, a sample with a moisture content of 1.2 $g/m^2$ correlates to an absorption maximum at 1490 nm of 0.2795, while a sample with a moisture content of 4 $g/m^2$ shows an absorption maximum of 0.3175. Accordingly, the baseline of the samples is shifted also to higher absorption values. For this reason, the interpretation of the NIR spectra is done by means of the multivariate data analysis (MDA) over the complete recorded spectral range of the NIR spectrum.

Suitable calibration models are established for further evaluation of the NIR spectra.

Figure 2A:
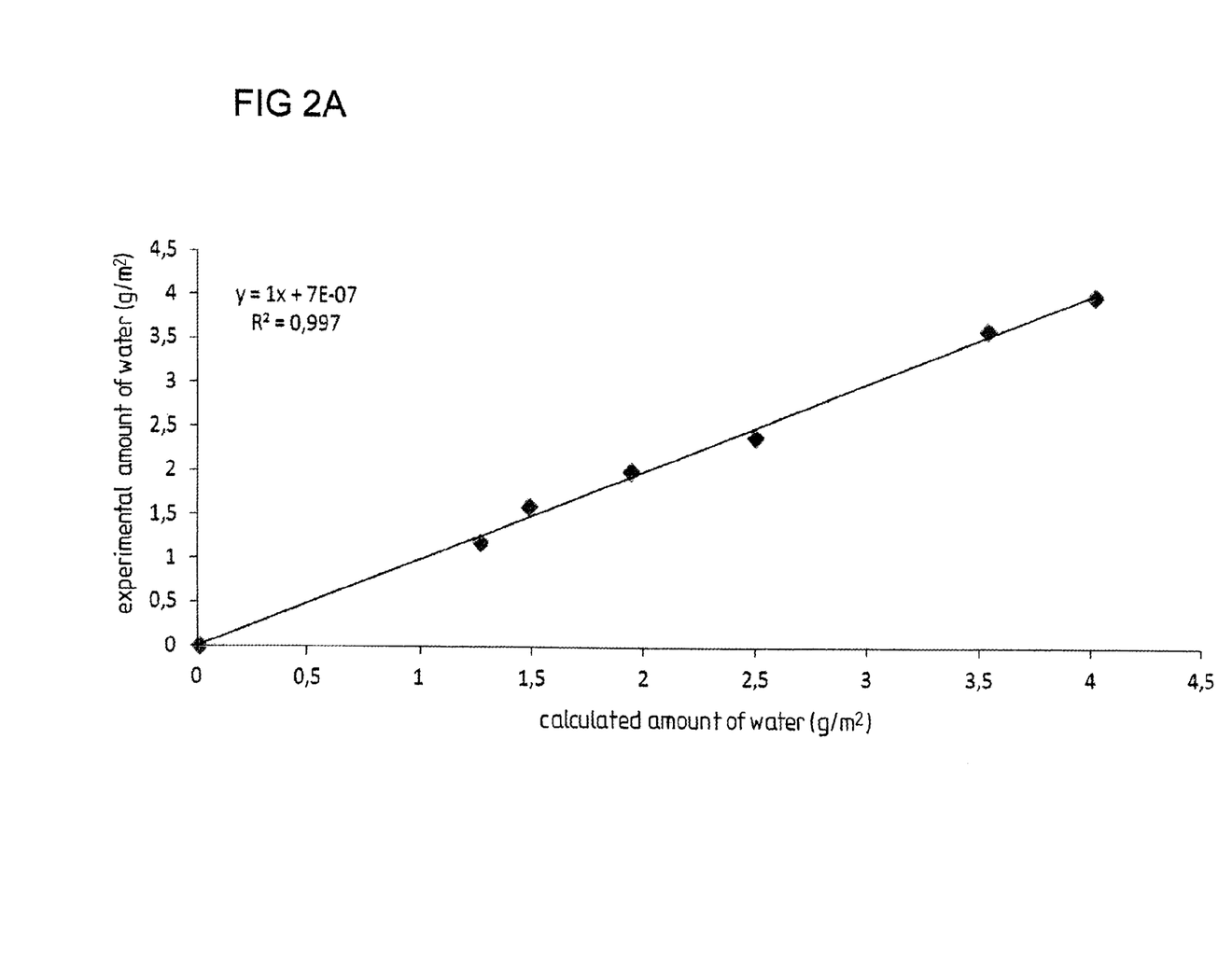
FIG. 2a is a diagram of a first PLS calibration model determined for a Darr sample of a carrier board provided with a resin layer according to the principles of the present invention.

Thus, the diagram of FIG. 2a shows a first calibration model for the NIR spectra of the reference samples of FIG. 1b (without Darr sample) that was determined by using partial least squares (PLS) regression.

This model is used for determining the residual moisture in the Darr sample. By using the first calibration model a moisture content is calculated for the Darr sample by the analysis program SIMCA-P. For this purpose, the partial least square (PLS) regression is used for establishing a calibration function, which describes a dependency between spectrum and moisture content. A moisture content of −2.9 $g/m^2$ is calculated as the moisture content of the Darr sample by the analysis program by using the established calibration function (see also table 2).

TABLE 2

Moisture content of the reference sample according to a first calibration model without considering the Darr sample

| Moisture experimental ($g/m^2$) | Moisture calculated ($g/m^2$) |
|---|---|
| 4.0 | 4.028204 |
| 3.6 | 3.546026 |
| 2.4 | 2.501772 |
| 2.0 | 1.946527 |
| 1.6 | 1.489633 |
| 1.2 | 1.27186 |
| 0 | 0.015972 |
| Unknown (Darr sample) | −2.906791 |

Subsequently, the amount of the moisture content of 2.9 g/m² for the Darr sample is added to all used moisture values of the calibration sample or reference sample and the moisture content of the Darr sample is set to zero. Based on these new calibration values of the moisture and the measured spectra a second calibration model is established by means of the partial least square (PLS) regression (FIG. 2b), which is now suitable for establishing a relationship between the measured NIR spectra of a resin layer on a carrier board to be measured and the NIR spectra of reference samples with known moisture content (see table 3).

TABLE 3

Moisture content of reference samples and unknown samples according to the second calibration model under consideration of the Darr sample

| Moisture experimental (g/m²) | Moisture calculated (g/m²) |
|---|---|
| 6.9 | 6.992321 |
| 6.5 | 6.264024 |
| 5.3 | 5.459239 |
| 4.9 | 4.860341 |
| 4.5 | 4.518459 |
| 4.1 | 4.119654 |
| 2.9 | 2.897086 |
| (Darrprobe) 0 | −0.01112 |
| Unknown (spectrum FIG. 1a) | 5.814462 |

Figure 2B:
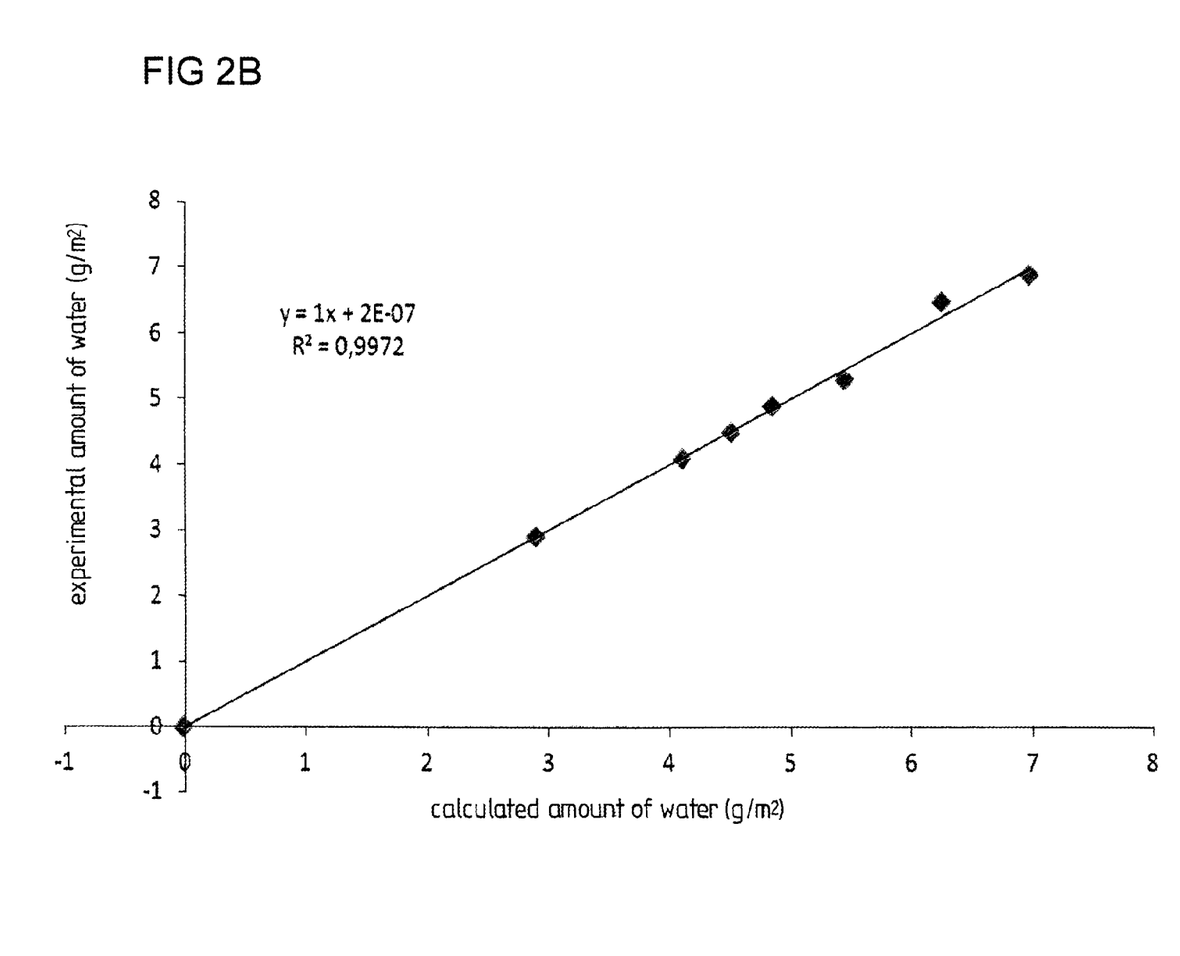
FIG. 2b is a diagram of a second PLS calibration model determined for reference samples according to the principles of the present invention.

By considering the PLS calibration model of linear regression shown in FIG. 2b the NIR spectrum determined for the above example is designated to a specific moisture content. Thus, in the present case the NIR spectrum of the example of FIG. 1a correlates to a moisture content of about 5.8 g/m².

The invention claimed is:

1. A method for determining the moisture content of at least one resin layer provided on at least one wooden board as carrier board, wherein between the at least one resin layer and the carrier board an NIR reflecting layer is provided, the method comprising:
  recording of at least one NIR spectrum of the at least one resin layer provided on the at least one carrier board using a NIR detector in a wavelength range between 500 nm and 2500 nm; and
  determining the moisture content of the resin layer by comparing the NIR spectrum recorded for the resin layer to be measured with at least one NIR spectrum recorded for at least one reference sample with known moisture content by means of a multivariate data analysis (MDA);
  wherein the at least one NIR spectrum recorded for the at least one reference sample with known moisture content was determined previously using the same NIR detector in a wavelength range between 500 nm and 2500 nm;
  wherein the method is conducted in a production line of the at least one wooden board, comprising: at least one application device, at least one drying device, at least one NIR detector, and
  wherein the at least one NIR detector is arranged after the applying device and the drying device; and
  wherein the moisture content of the at least one resin layer is adjusted in the production line based on the determined moisture content of the resin layer.

2. The method according to claim 1, wherein the at least one wooden board is at least one of the following: a medium density fiber (MDF), a high density fiber (HDF), an oriented strand (OSB) board, a plywood panel, a cement fiber board, a gypsum fiber board, a wood-plastic-board or any combination thereof.

3. The method according to claim 1, wherein the reference sample with known moisture content comprises at least one, resin layer applied to a carrier board, wherein the resin layer and the carrier board of the reference sample are of the same kind of the sample of resin layer and carrier board to be measured.

4. The method according to claim 3, wherein the resin layer is pre-dried.

5. The method according to claim 1, wherein the resin layer to be measured comprises at least one of the following: a formaldehyde containing resin, a melamine formaldehyde resin, a urea formaldehyde resin or mixtures thereof, a polyurethane, an acrylate or any combination thereof.

6. The method according to claim 1, wherein the resin layer to be measured comprises at least one of the following: wear resistant particles, natural fibers, synthetic fibers, further additives or any combination thereof.

7. The method according to claim 1, wherein the resin layer to be measured comprises a plurality of layers.

8. The method according to claim 7, wherein the resin layer to be measured comprises three layers, wherein in one of the three layers of the resin layer wear resistant particles are present, in a second of the three layers natural and/or synthetic fibers are present and in a third of the three layers again wear resistant particles are present.

9. The method according to claim 1, wherein the determination of the moisture content of the resin layer is carried out after applying the resin layer to the carrier board and a drying step in a drying segment using the at least one NIR detector.

10. The method according to claim 1, wherein the determination of the moisture content of the resin layer takes place after applying and drying at least one resin layer, respectively.

11. The method according to claim 1, wherein the at least one NIR reflecting layer comprises a layer construction of a plurality of NIR reflecting layers.

12. The method according to claim 11, wherein the at least one NIR reflecting layer comprises a layer construction of at least one of the following: two NIR reflecting layers, three NIR reflecting layers, and four NIR reflecting layers.

13. The method according to claim 1, wherein the at least one NIR reflecting layer comprises at least one of the following: at least one first resin layer, at least one white priming layer, at least one decor layer printed onto the wooden board, at least one protective layer or any combination thereof.

14. The method according to claim 13, wherein the at least one decor layer printed on the wooden board is a water-based pigmented printing color, which is applied in gravure printing or digital printing.

15. The method according to claim 14, wherein at least one protective layer of a resin is provided on the at least one decor layer printed on the wooden board.

16. The method according to claim 13, wherein at least one protective layer of a resin is provided on the at least one decor layer printed on the wooden board.

17. The method according to claim 1, wherein the resin layer to be measured is arranged on the upper side and/or lower side of the carrier board.

18. A device for determining the moisture content of at least one resin layer arranged on a wooden board as carrier board according to the method according to claim 1, wherein the device comprises at least one application device, at least one drying device and at least one NIR detector, wherein the at least one NIR detector is arranged in a processing direction after the applying device and the drying device.

19. The method according to claim 1, wherein the wavelength range is between 700 nm and 2000 nm.

20. The method according to claim 1, wherein the wavelength range is between 900 nm and 1700 nm.

* * * * *